United States Patent

Hulli

(10) Patent No.: US 8,522,383 B2
(45) Date of Patent: Sep. 3, 2013

(54) OPHTHALMIC TREATMENT BRUSH

(76) Inventor: Nelson Hulli, Toronto (CA)

( * ) Notice: Subject to any disclaimer, the term of this patent is extended or adjusted under 35 U.S.C. 154(b) by 146 days.

(21) Appl. No.: 13/173,099

(22) Filed: Jun. 30, 2011

(65) Prior Publication Data

US 2012/0000022 A1    Jan. 5, 2012

Related U.S. Application Data

(60) Provisional application No. 61/361,066, filed on Jul. 2, 2010.

(51) Int. Cl.
*A46B 13/00* (2006.01)
(52) U.S. Cl.
USPC .................................................. 15/28
(58) Field of Classification Search
USPC ............... 15/22.1, 22.2, 28, 53.1, 105, 106; 606/5, 107, 161
See application file for complete search history.

(56) References Cited

U.S. PATENT DOCUMENTS

| | | | | |
|---|---|---|---|---|
| 1,874,467 | A * | 8/1932 | Doll | 15/167.1 |
| 5,649,943 | A * | 7/1997 | Amoils | 606/161 |
| 2005/0011024 | A1* | 1/2005 | Ping et al. | 15/22.1 |
| 2008/0083077 | A1* | 4/2008 | Alexander et al. | 15/53.1 |

* cited by examiner

*Primary Examiner* — Robert Scruggs
(74) *Attorney, Agent, or Firm* — Gerard F. Dunne

(57) ABSTRACT

A brush for use with a rotating motor device comprises a collar and a brush-head. The collar has a first open end and a second securing end. The securing end of the collar has a polygonal opening adapted for securely mating with a corresponding polygonal rotating shaft of a rotating motor device, such that when second end of the collar is secured to the rotating shaft, rotation of the shaft causes corresponding rotation of the collar. The brush-head comprises a plurality of bristles cylindrically bundled, said cylindrical bundle having a first fused end and a second loose end, wherein the bristles are securely fused to together at the fused end and the bristles are unattached to each other at the loose end, and the bristles at the loose end define a generally concave brush face wherein the bristles in the center portion are shorter than the bristles in the perimeter portion. The fused end of brush-head is adapted to slide snugly within the open end of the collar such that rotation of the collar causes corresponding rotation of the brush-head.

1 Claim, 2 Drawing Sheets

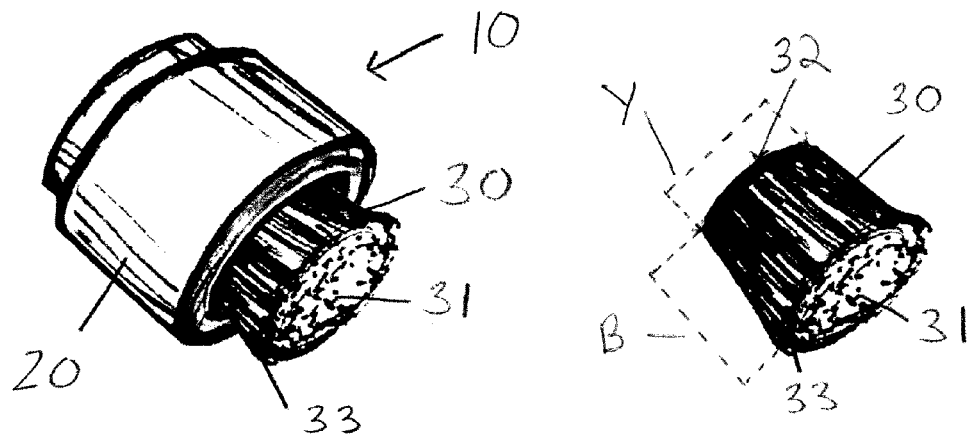
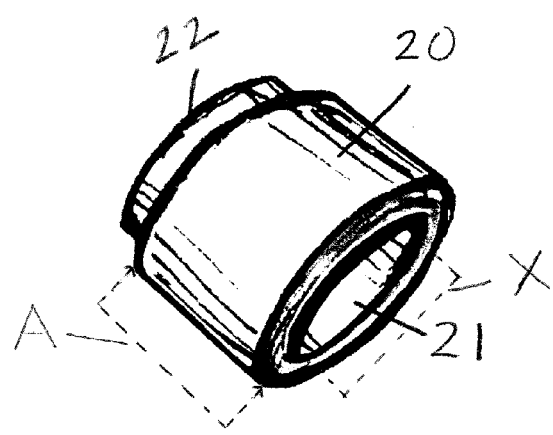
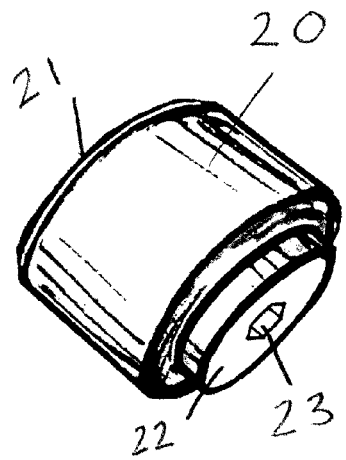
Fig. 1
Fig. 2
Fig. 3
Fig. 4

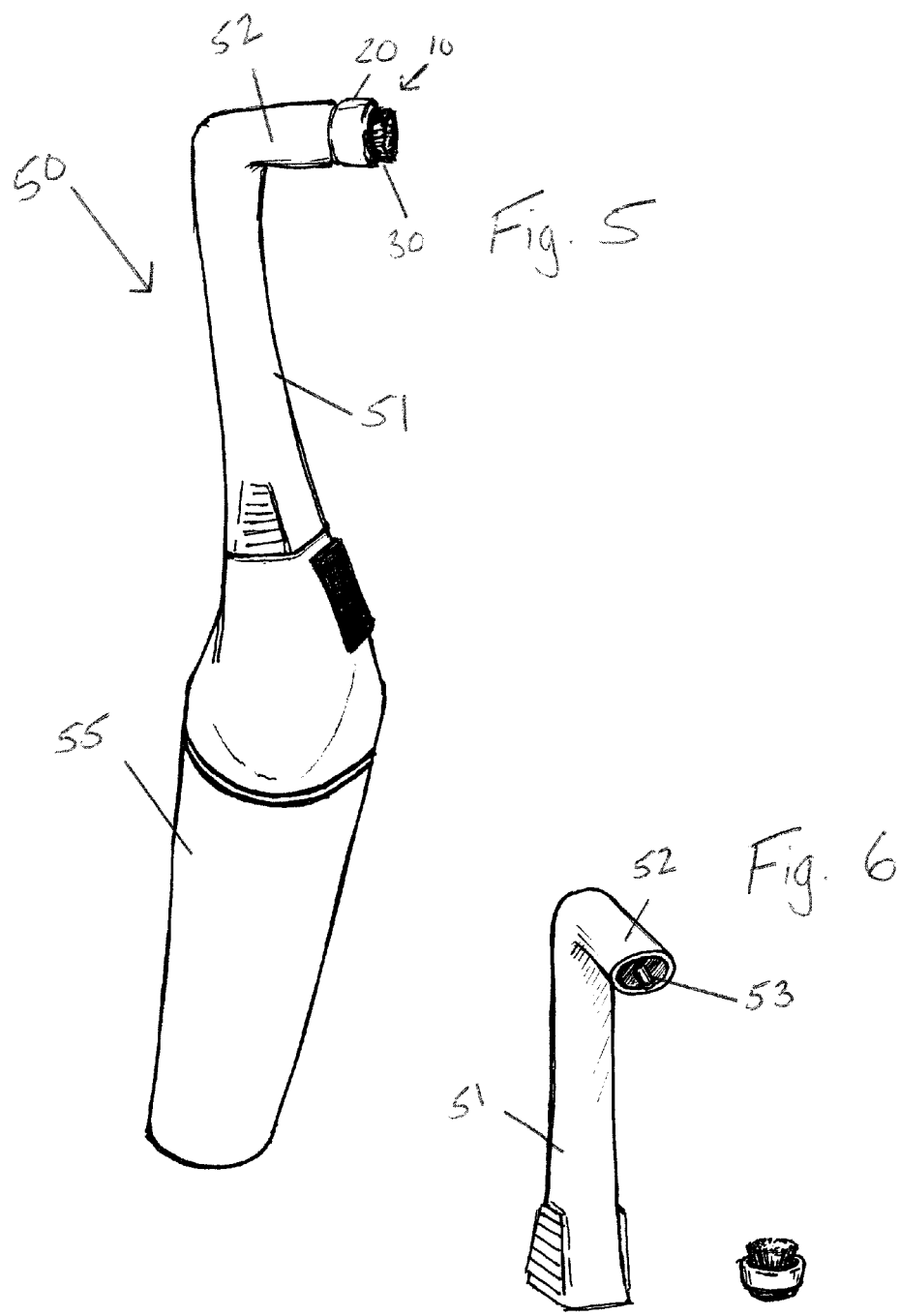

US 8,522,383 B2

OPHTHALMIC TREATMENT BRUSH

RELATED APPLICATION

The application claims priority of provisional patent application, Ser. No. 61/361,066 filed Jul. 2, 2010.

FIELD OF THE INVENTION

The present invention relates to a brush for use in pre-surgery ophthalmic treatment. The soft-brush is designed to gently remove the soft cellular epithelium from the hard fibrous cornea prior to ophthalmic processes, such as vision corrective procedures.

BACKGROUND OF THE INVENTION

Laser-based surgical techniques have become increasingly more common for vision correction, and the removal of the cellular epithelium layer of the relatively hard fibrous cornea from the surface of the eyes is necessary in the preparation of such corrective surgeries.

U.S. Pat. No. 5,649,943 ("Amoils") discloses a device and method for removing the cellular epithelium layer. The present invention is a refinement and improvement of the brush used in the device and of the methods disclosed in Amoils, and accordingly applicant incorporates herewith the disclosure shown in the Amoils patent.

Prior devices, such as Amoils, disclose a brush-head attaching directly to the rotating motor device, however the present invention allows for a two-piece brush system where a collar is attached directly to the rotating motor device, and a brush-head is securely inserted within the collar. This brush device allows for more versatility and efficiency by allowing a variety of brush-heads to be interchanged within a given collar, without removal of said collar.

SUMMARY OF THE INVENTION

The present invention is a brush using a two-piece construction, a collar and a brush-head. The brush of the present invention is designed to overcome the problem of slipping when using a two-piece brush, so that the collar does not simply spin, while the brush-head remains in place.

The collar of the present invention has a polygonal opening at the base designed to be compatible with the rotating polygonal shaft of a rotating motor device, such as that disclosed by Amoils. Said polygonal opening fits securely over the polygonal shaft attached to the rotating motor, such that when the motor is activated, the collar is caused to rotate. The other end (the top) of the collar, is an open cylindrical cavity of a diameter designed to precisely fit a line of specific sized brush-heads, and with a depth that is less than the length of the corresponding brush-heads, in order to allow a portion of the brush-head to protrude above the collar. It should be understood that a variety of brush-head and collar sizes can be accommodated according to their respective diameters.

The brush-head of the present invention is comprised of a plurality of fine bristles bunched together in a cylindrical arrangement, and fused at one end, defining a diameter precisely designed to fit securely within the respectively sized collar. When in use, the fused end is inserted into the cylindrical cavity of the collar, where it is held securely in place. Accordingly, the diameter of the brush-head is nearly identical to that of the cavity in the collar, however it is ever-so-slightly smaller so that the brush-head will fit inside the cavity but it will be held snugly in place.

The use of the fused end and the precise mating design of the brush-head and collar avoid any slippage when the collar is rotating, such that when the rotating motor device is activated, the collar and in-turn the brush-head will rotate accordingly.

Different brushes are required for Myopic and Hyperotic corrective surgeries. And one can also imagine a need for variations in the convex curvature of the loose-end of the bristles in order to allow the brush to match the possible variations in the curvature of the patients' corneas. Accordingly, easy interchangeability of the brush-heads is advantageous in the field, and the present invention allows for easy substitution of one brush-head or another, while the collar remains fixed in place to the rotating motor device.

BRIEF DESCRIPTION OF THE DRAWINGS

The attached figures illustrate an Ophthalmic Treatment Brush according to the present invention.

FIG. 1 illustrates a perspective a view of one embodiment of the brush of the present invention;

FIG. 2 illustrates a perspective a view of one embodiment of the brush-head of the present invention;

FIG. 3 illustrates a perspective a view showing the open cavity end of one embodiment of the collar of the present invention;

FIG. 4 illustrates a perspective a view showing the securing base of one embodiment of the collar of the present invention;

FIG. 5 illustrates a perspective a view of a rotating motor device with the brush of the present invention;

FIG. 6 illustrates a perspective a view of the neck of a rotating motor device the brush of the present invention is adapted for use with;

DETAILED DESCRIPTION OF PREFERRED EMBODIMENTS

According to the present invention, as detailed in FIGS. 1 through 4, a brush (10) for use in ophthalmic treatment is comprised of a brush-head (30) and a separate color (20). The brush is adapted for use with a rotating motor device (50), as shown in FIGS. 5 and 6. The rotating motor device (50) generally comprises a stem (51), with a bent neck (52), secured to a base (55). Neck (52) terminates in a rotating shaft (53) that is adapted to hold and secure a brush, such as the brush (10) of the present invention.

The brush-head (30) is comprised of a cylindrical bundle of bristles (33) fused together at one end (32) and loose on the other end (31). Said cylindrical bundle defined by a diameter (Y) and a height (B). The fused end (32) of the brush forms a uniform end, and the loose end (31) of the brush is comprised of numerous individual bristles (33). The bristles (33) on the loose end (31) form a generally convex surface, designed to form to the contour of the corneal surface of the eye, whereas the bristles (33) on the fused end (32) are fused together to form a uniform, generally flat surface designed to be inserted into the open end (21) of collar (20).

The collar (20) is a rigid molded piece having a generally cylindrical shape with a first end (21) and second end (22). The second end (22) including a means for attaching (23) the collar to the rotating shaft (53) of a rotating motor device (50), such as the device disclosed in Amoils, or as shown in FIGS. 5 and 6. Said means is a polygonal opening (23) designed specifically to mate with the securing end of a rotating shaft (53). In the preferred embodiment of collar (20), the second end (22) has a hexagonal opening (23), which is designed to conform with a corresponding hexagonal rotating shaft (53), at the end of the a rotating motor device (50). It should be understood that the opening (23) and the rotating shaft (53) can be any corresponding non-circular polygonal shape, such as a triangle, rectangle, or star-shape.

The first end (21) of the collar (20) includes a recessed cylindrical cavity designed to receive and securely hold the fused end (32) of the brush-head (30) in place. Said cylindrical cavity defined by a diameter (X) and a depth (A). The cavity at the first end (21) and the brush-head (30) are designed cylindrically with matching diameters (X and Y respectively), such that any brush-head (30) of the appropriate diameter (Y) is easily interchangeable with said collar (20).

What is claimed is:

1. A brush for use with a rotating motor device, said brush comprising a collar and a removable brush-head;

said collar comprising a first open end and a second securing end, said first open end having a cylindrical cavity defined by a diameter (X) and a depth (A,) and said second securing end having a polygonal opening adapted for securely mating with a corresponding polygonal rotating shaft of a rotating motor device, such that when second end of said collar is secured to said rotating shaft, rotation of said shaft causes corresponding rotation of said collar; and said removable brush-head comprising a plurality of bristles cylindrically bundled, said cylindrical bundle having a first fused end and a second loose end, and said cylindrical bundle defined by a diameter (Y) and perimeter height (B,) wherein the bristles are securely fused to together at said fused end and the bristles are unattached to each other at said loose end; the bristles at said loose end define a generally concave brush face wherein the bristles in the center portion are shorter than the bristles in the perimeter portion;

wherein said cavity diameter (X) and said bundle diameter (Y) are nearly identical, with bundle diameter (Y) being slightly shorter than cavity diameter (X,) such that said cylindrical bundle is capable of being removably secured within said cylindrical cavity such that when the device is in use, rotation of the collar causes corresponding rotation of said brush-head, and wherein said cavity depth (A) is shorter than bundle perimeter height (B,) such that when said cylindrical bundle slides snugly within said cylindrical cavity, the loose end of said brush-head extends beyond the open end of said collar.

* * * * *